(12) United States Patent
Weiss

(10) Patent No.: US 12,292,488 B2
(45) Date of Patent: May 6, 2025

(54) ARRANGEMENT AND METHOD FOR DETERMINING THE POSITION OF AN INVASIVE DEVICE

(71) Applicant: KONINKLIJKE PHILIPS N.V., Eindhoven (NL)

(72) Inventor: Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 109 days.

(21) Appl. No.: 18/017,889

(22) PCT Filed: Jul. 9, 2021

(86) PCT No.: PCT/EP2021/069132
§ 371 (c)(1),
(2) Date: Jan. 25, 2023

(87) PCT Pub. No.: WO2022/022986
PCT Pub. Date: Feb. 3, 2022

(65) Prior Publication Data
US 2023/0273279 A1 Aug. 31, 2023

(30) Foreign Application Priority Data
Jul. 28, 2020 (EP) .................................... 20188055

(51) Int. Cl.
*G01R 33/28* (2006.01)
*A61B 6/00* (2024.01)
(Continued)

(52) U.S. Cl.
CPC .............. *G01R 33/285* (2013.01); *A61B 6/12* (2013.01); *A61B 6/5247* (2013.01); *A61B 2034/2061* (2016.02)

(58) Field of Classification Search
CPC .. G01R 33/285; G01R 33/286; G01R 33/287; A61B 6/12; A61B 6/5247;
(Continued)

(56) References Cited

U.S. PATENT DOCUMENTS 7,653,426 B2    1/2010  Yatsuo et al.
2010/0056904 A1  3/2010  Saunders et al.
(Continued)

FOREIGN PATENT DOCUMENTS

WO    2012056386 A1    5/2012
WO    2013001388 A1    1/2013
(Continued)

OTHER PUBLICATIONS

Dumoulin CL, Souza SP, Darrow RD. Real-time position monitoring of invasive devices using magnetic resonance. Magn Reson Med 1993;29: 411-415.
(Continued)

*Primary Examiner* — Yi-Shan Yang
*Assistant Examiner* — Nicholas A Robinson

(57) ABSTRACT

For the field of determining the position of an invasive device (1) a solution for improving the localization of the invasive device (1) is specified. This is achieved by an arrangement and a method for determining the position of an invasive device (1), wherein an optical shape sensing system for sensing a position and/or shape of the invasive device (1) is provided, wherein the system is arranged to localize at least one point $P_i$ on the invasive device (1) at a position $x_i$, $y_i$, $z_i$, with some error margin ($2\Delta x_i$, $2\Delta y_i$, $2\Delta z_i$) in a region of interest (3), localizing and reconstructing at least one point $P_i$ on the invasive device (1) at a position $x_i$, $y_i$, $z_i$, with some error margin ($2\Delta x_i$, $2\Delta y_i$, $2\Delta z_i$) in a region of interest (3) by the optical shape sensing system. An MRI system is also provided for measuring the position $x_i$, $y_i$, $z_i$ of the point
(Continued)

$P_i$ on the invasive device (1) within the error margin in the region of interest at least in one spatial direction by the MRI system, wherein a signal of the magnetization in the error margin ($2\Delta x_i$, $2\Delta y_i$, $2\Delta z_i$) is read out by the MRI system and a position of the invasive device (1) is determined based on the signal. The position $x_i$, $y_i$, $z_i$, of the point $P_i$ on the invasive device (1) in the region of interest (3) determined by the optical shape sensing system is corrected with the $x_i$, $y_i$, $z_i$, of the point $P_i$ on the invasive device (1) in the region of interest (3) determined by the MRI system by a calculating system to an actual position of the point $P_i$ on the invasive device (1).

13 Claims, 2 Drawing Sheets

(51) Int. Cl.
*A61B 6/12* (2006.01)
*A61B 34/20* (2016.01)

(58) Field of Classification Search
CPC .... A61B 2034/2061; A61B 2090/3954; A61B 2090/3958; A61B 5/065; A61B 2562/0266
See application file for complete search history.

(56) References Cited

U.S. PATENT DOCUMENTS

| 2011/0257512 A1* | 10/2011 | Krueger | A61B 5/0263 601/2 |
| 2014/0155737 A1* | 6/2014 | Manzke | A61B 8/462 600/417 |
| 2016/0171714 A1 | 6/2016 | Ekin et al. | |

FOREIGN PATENT DOCUMENTS

| WO | 2013024418 A1 | 2/2013 |
| WO | 2014053934 A1 | 4/2014 |
| WO | 2017139621 A1 | 8/2017 |

OTHER PUBLICATIONS

Weiss S, Vernickel P, Schaeffter T, Schulz V, Gleich B. Transmission Line for Improved RF Safety of Interventional Devices. Magn Reson Med 2005;54:182-189.

International Search Report and Written Opinion from PCT/EP2021/069132 mailed Sep. 28, 2021.

Elayaperumal et al "Autonomous Real-Time Interventional Scan Plane Control with a 3-D Shape—Sensing Needle" IEEE Tans. Med. Imaging 2014 33(11) p. 2128-2139.

Koushik et al "Vessel Based Registration of an Optical Shape Sensing Catheter for MR Navigation" Int. Journal of Computer Assisted Radiology and Surgery, vol. 11, No. 6 Mar. 16, 2016.

* cited by examiner

ARRANGEMENT AND METHOD FOR DETERMINING THE POSITION OF AN INVASIVE DEVICE

CROSS REFERENCE TO RELATED APPLICATIONS

This application is a U.S. national phase application of International Application No. PCT/EP2021/069132 filed on Jul. 9, 2021, which claims the benefit of EP Application Serial No. 20188055.6 filed on Jul. 28, 2020 and is incorporated herein by reference.

FIELD OF THE INVENTION

The invention relates to the field of determining the position of an invasive device and in particular of determining the position of an invasive device based on optical shape sensing supported by diagnostic imaging.

BACKGROUND OF THE INVENTION

MR-guidance of intravascular procedures is a promising approach in many applications due to the superior soft tissue contrast of MRI compared to conventional fluoroscopy or ultrasound guidance. While the variety of contrasts and physiological parameters is a big advantage in MR, visualization and localization of invasive devices like catheters is associated with additional technical effort and safety concerns unlike in fluoroscopy or ultrasound. MR devices can either be visualized passively by a contrast due to the absence of water in the invasive device, by a contrast due to contrast agent present in the invasive device, or actively by the integration of wired μ-MR receive coils in the invasive device.

Fiber-optical shape sensing allows sensing the shape of a flexible compound optical fiber in 3D with high temporal and spatial resolution. It is based on optical sensing of the strain of individual optical cores along the compound fiber, either by fiber Bragg gratings or by Rayleigh scattering. The known relative configuration of the cores allows reconstruction the shape of the compound fiber from the strain data.

Passive MR visualization requires the invasive device to be contained in the real-time MR imaging slice to be visible. Hence, both, the invasive device and the imaging slice must be maneuvered in turns, which is clearly inferior to the rapid and uncomplicated visualization in fluoroscopy. The imaging slice must be shifted and angulated to depict at least a part of the shaft of the invasive device. Mostly, the 3D invasive device configuration allows to visualize only a short part of the shaft within one slice. For these reasons, passive visualization is rarely applied for invasive devices, rather for rigid devices as needles and ablation devices.

Active MR tracking was demonstrated pre-clinically already more than a decade ago but could not be applied clinically for a long time, because the wiring of inside the invasive device represents a safety hazard due to potential RF heating of the invasive device during MR imaging. This issue has been solved by the introduction of miniature transformers into the wiring. However, in practice, active invasive device tracking can only localize two or maximally three points along the invasive device because each point has to be equipped with a and requires a separate cable in the shaft of the invasive device with a diameter of about 500 μm. This is a major drawback in comparison to competing means for invasive device visualization in other modalities including electromagnetic localization systems which do display the entire shaft or at least a large part of the distal shaft of the invasive device. Moreover, even the latest implementation of the MR active tracking technology still has a relatively high failure rate due to breaking of internal wires, mostly due to repeated sharp bending of the invasive device.

The fiber-optical real shape (FORS) technology is based on the measurement of mechanical strain along very many points of the fiber, and the shape is reconstructed by the integration of these strain values. Errors in the individual strain measurements thus add up, so that the shape error increases from zero at a known fixed point at the proximal end of the fiber towards the tip of the fiber. The current implementation of the FORS technology achieves a tip localization accuracy (distance to true position) of 6 mm over a 1.8 m long fiber. Systematic effects as pulling forces on the fiber cause a large part of this error. The precision (standard variation of repeated measurements in a fixed fiber configuration) is about 1 mm at 50 Hz, which is comparably small. However, an overall tip localization accuracy of 6 mm is still too large for many invasive device or catheter applications, especially for cardiac catheter ablations, which are performed with catheters of a diameter between 1.3 mm and 2 mm.

The US-patent application US2014/155737 concerns a curved multiplanar rendering (MPR) of 3D reconstructed MR image data based on the shape of a catheter measured by way of fibre optical shape (FOS) sensing.

SUMMARY OF THE INVENTION

It is an object of the invention to provide an arrangement and a method for determining the position of an invasive device based on optical shape sensing supported by diagnostic imaging, for example by magnetic resonance imaging such that the accuracy of the determination of the position by optical shape sensing is improved.

According to the invention, this object is addressed by the subject matter of the independent claims. Preferred embodiments of the invention are described in the sub claims.

Therefore, according to the invention, an arrangement for determining the position of an invasive device is provided, the arrangement comprising: at least one invasive device, at least one optical shape sensing system, wherein the optical shape sensing system is configured for determining a position and/or shape of the invasive device the optical shape sensing system further being arranged to localize and reconstruct at least one point $P_i$ on the invasive device at a position $x_i$, $y_i$, $z_i$, with some error margin in a region of interest, a diagnostic imaging system, for example a magnetic resonance imaging (MRI) system, wherein the MRI system is configured to measure the position $x_i$, $y_i$, $z_i$ of the point $P_i$ on the invasive device within the error margin in the region of interest at least in one spatial direction, at least one calculating system wherein the calculating system is configured to correct the position $x_i$, $y_i$, $z_i$, of the point $P_i$ on the invasive device determined by the optical shape sensing system by the position $x_i$, $y_i$, $z_i$, of the point $P_i$ on the invasive device determined by the MRI system to an actual position of the invasive device.

The basic idea of the present invention is that FORS technology is integrated with a diagnostic imaging system, such as the MRI-system and FORS data are augmented by dedicated MR imaging such that the accuracy of shape sensing is improved to a fraction of the diameter of the invasive device along the full invasive device. FORS is used to localize isolated and predefined points $P_i$ on the invasive device in 3D. Dedicated MR projection and imaging sequences are used to cover these regions of interest with high resolution but very limited FOV and therefore very short acquisition time. Dedicated reconstructions of these MR data resolve the exact locations on the points, which is used to correct the overall shape reconstruction.

According to a preferred embodiment the magnetic resonance imaging (MRI) system is further configured to excite a magnetization in the error margin in the region of interest at least in one spatial direction by exciting a z-slice and/or a y-slice and/or a x-slice centered at the point $P_i$ at the position $x_i$, $y_i$, $z_i$ and perpendicular to a direction vector $n_i$ with the MRI system, the MRI system being arranged to read out a signal of the excited z-slice and/or a y-slice and/or a x-slice with a readout gradient along the x-direction and/or along the y-direction and/or along the z-direction, the MRI system further being arranged to perform a scheme for finding a signal suppression in the signal of the excited z-slice and/or a y-slice and/or a x-slice to determine a position $x_i$, $y_i$, $z_i$, of the point $P_i$ on the invasive device based on the signal.

According to another preferred embodiment the invasive device comprises at least one MR marker along the extension of the invasive device. To simplify the extraction of the location of the point $P_i$ on the invasive device from the MR data, the invasive device may be equipped with MR markers at the point $P_i$.

Preferably, the MR marker is selected from the list of the following MR marker: paramagnetic agents, ferromagnetic agents, ferrimagnetic agents, antiferromagnetic agents, resonant pickup radiofrequency (RF) coils, inductively coupled RF coils. For example, passive or active MR marker can be provided.

In another aspect of the invention, the object is achieved by a method for determining the position of an invasive device the method comprising the following steps:
 providing an invasive device,
 providing a magnetic resonance imaging (MRI) system,
 providing an optical shape sensing system for sensing a position and/or shape of the invasive device, the system being arranged that to localize at least one point $P_i$ on the invasive device at a position $x_i$, $y_i$, $z_i$, with some error margin in a region of interest,
 localizing and reconstructing at least one point $P_i$ on the invasive device at a position $x_i$, $y_i$, $z_i$ in the region of interest by the optical shape sensing system,
 measuring the position $x_i$, $y_i$, $z_i$ of the point $P_i$ on the invasive device within the error margin in the region of interest at least in one spatial direction by the MRI system,
 reading out a signal of the magnetization in the error margin by the MRI system,
 determining a position of the invasive device based on the signal,
 correcting the position $x_i$, $y_i$, $z_i$, of the point $P_i$ on the invasive device in the region of interest determined by the optical shape sensing system with the position $x_i$, $y_i$, $z_i$, of the point $P_i$ on the invasive device in the region of interest determined by the MRI system by the calculating system.

In brief, the invention concerns to determine the position of an invasive device on the basis of a combination of (i) optical shape sensing and (ii) diagnostic imaging, in particular magnetic resonance imaging, x-ray imaging or computed tomography. According to the invention a relatively less accurate determination of the position of the invasive device is made by way of optical shape sensing, this initial position is then employed to arrange for a radio frequency (RF) excitation of a limited volume (slab) around the initial position and a more accurate determination of the position of the invasive device in the slab is derived from the MR-image information for the RF excited slab. In a particular embodiment this is done by projections of the magnetic resonance signals form the slab in three directions which returns to position of the invasive device in the slab. This determination makes use of the fact that the MR response of the material of the invasive device is different from the surrounding (tissue, mainly water) in the slab.

The method concerns the operation of the technical device as described above, namely how the position of the invasive device is determined by computer with the aid of the optical shape sensing system and the magnetic resonance imaging (MRI) system. With this method, the position and orientation of the invasive device is determined optically and by MRI, i.e. non-invasively. There is no functional link and hence no physical causality between its constituent steps carried out in relation to the invasive device and a surgical treatment produced on the body by that device. Therefore, the method and the effects produced by the device on a human or animal body does not qualify at all as a method for treatment. Furthermore, no procedural step for surgical treatment of the body is included in the method nor is any such step covered by the method. In particular the method does not comprise or encompasses an invasive step representing a substantial physical intervention on the body which requires professional medical expertise to be carried out and which entails a substantial health risk even when carried out with the required professional care and expertise. In particular, it can be provided that the method is not applied to a human or animal body.

According to a preferred embodiment, the step of measuring the position $x_i$, $y_i$, $z_i$ of the point $P_i$ on the invasive device within the error margin in the region of interest comprises the steps of
 exciting a z-slice and/or a y-slice and/or a x-slice centered at the point $P_i$ at the position $x_i$, $y_i$, $z_i$ and perpendicular to a direction vector $n_i$ of the invasive device with the MRI system,
 reading out a signal of the excited z-slice and/or a y-slice and/or a x-slice within the error margin by the MRI system,
 determining a position of the invasive device based on the signal.

Preferably, the step of reading out a signal of the magnetization in the error margin, comprises the step of reading out a signal of the excited z-slice and/or a y-slice and/or a x-slice with a readout gradient along the x-direction and/or along the y-direction and/or along the z-direction.

More preferably, the thickness of the z-slice and/or y-slice and/or x-slice is between two to three times the thickness of the invasive device.

Preferably, the step of determining a position of the invasive device based on the signal comprises the step of performing a scheme for signal suppression of the signal of the excited z-slice and/or a y-slice and/or a x-slice outside a region $x_i-\Delta x_i$ to $x_i+\Delta x_i$ and/or $y_i-\Delta y_i$ to $y_i+\Delta y_i$ and/or $z_i-\Delta z_i$ to $z_i+\Delta z_i$ based on the localizing and reconstructing of the at least one point $P_i$ on the invasive device at the position $x_i$, $y_i$, $z_i$ by the optical shape sensing system.

According to another preferred embodiment, the step of performing a scheme for signal suppression of the signal of the excited z-slice and/or a y-slice and/or a x-slice is performed by a spin echo scheme comprising the following steps:
 selective exciting a z-slice and/or y-slice and/or x-slice, performing a selective y-slice refocusing pulse with a slice center at $y_i$ and a slice thickness of $2\Delta y_i$ and/or performing a selective x-slice refocusing pulse with a slice center at $x_i$ and a slice thickness of $2\Delta x_i$ and/or performing a selective z-slice refocusing pulse with a slice center at $z_i$ and a slice thickness of $2\Delta z_i$ reading out the signal along the x-direction, and/or z-direction and/or y-direction.

Preferably, the step of performing a scheme for signal suppression of the signal of the excited z-slice and/or a y-slice and/or a x-slice is performed by a saturation scheme comprising the following steps:

exciting and spoiling a signal in a region outside $y_i-\Delta y_i$ to $y_i+\Delta y_i$ and/or $x_i-\Delta x_i$ to $x_i+\Delta x_i$ and/or $z_i-\Delta z_i$ to $z_i+\Delta z_i$, selective exciting a z-slice and/or y-slice and/or x-slice, reading out the signal along the x-direction and/or z-direction and/or y-direction.

Preferably, the step of performing a scheme for finding a signal suppression in the signal of the excited z-slice and/or a y-slice and/or a x-slice is performed by a 2d-excitation scheme comprising the following steps:

exciting a column of a signal along x-direction and/or y-direction and/or z-direction by a 2d-pulse centered at the point $P_i$ at the position $x_i$, $y_i$, $z_i$.

Preferably, the step of localizing and reconstructing at least one point $P_i$ on the invasive device at a position $x_i$, $y_i$, $z_i$ by the optical shape sensing system, comprises the step of localizing and reconstructing at least one point $P_i$ on the invasive device, wherein the invasive device comprises at least one MR marker along the extension of the invasive device.

Preferably, the step of localizing and reconstructing at least one point $P_i$ on the invasive device at a position $x_i$, $y_i$, $z_i$, by the optical shape sensing system comprises the step of localizing and reconstructing a point $P_i$ at the tip point of the invasive device and/or at least at one point $P_i$ along a shaft of the invasive device.

More preferably, the step of localizing and reconstructing at least one point $P_i$ on the invasive device at a position $x_i$, $y_i$, $z_i$, comprises the step of firstly localizing the tip point of the invasive device, then localizing and reconstructing a point at half the length of the invasive device, then at a quarter the length of the invasive device and so forth as in a half-interval search.

According to an embodiment of the present invention, when the step of exciting a magnetization in the error margin in the region of interest has been performed in a first spatial direction by the MRI system the method comprises the step of exciting a magnetization in the error margin in the region of interest in at least another spatial direction.

In another aspect of the invention, the object is achieved by a computer program product comprising instructions which, when the program is executed by a computer, cause the computer to carry out the steps of the method as described above.

In a still further aspect of the invention, the object is achieved by a software package for a magnetic resonance (MR) imaging system, whereby the software package contains instructions for controlling a magnetic resonance imaging (MRI) system as described above.

Further implementations of the invention may make use of diagnostic imaging modalities, such as computed tomography or x-ray imaging. Optical shape sensing provides the device tip position within an error margin that represents a 3D volume which may be denoted as V. Optical shape sensing also provides the orientation of the tip section of the device which may be denoted with orientation vector k. It is proposed to use this knowledge to improve detection of the exact tip position in X-ray or CT by following embodiments.

In an embodiment of the invention based on x-ray imaging, it is proposed to project volume V to the X-ray image, effectively creating a 2D region of interest in this image (ROI). It is proposed to limit the range for searching the device tip to this ROI. Some extra margin depending on known size of the device may be added. This makes sure that the ROI fully covers the outer perimeter of the device. Already this simple measure will greatly improves robustness of detection of the device tip regarding increased sensitivity and lower false positive rate (increased specificity).

For the device detection itself any image processing algorithm may be used to find the device within the ROI, but preferably also the known orientation vector k and the size of the device may be used. As one embodiment, line filters are used to enhance any linear structures in the ROI that correspond to the projection k' of orientation k onto the image plane. Having identified the very line structure that corresponds to the device, a further filter may be used to exactly determine the end of the line along direction k', i.e. the device tip.

In an embodiment of the invention based on computed tomography (CT) it is proposed to firstly use the longitudinal (z)-range of the volume V. The search range of the device may be limited to the corresponding z-range of the detection/reconstruction volume of CT. Secondly, similarly as in the embodiment for X-ray, is exploited that the orientation k is known, here by directly enhancing line structures along k with a filter. Finally, the end of the line along k may be searched to detect the tip position.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
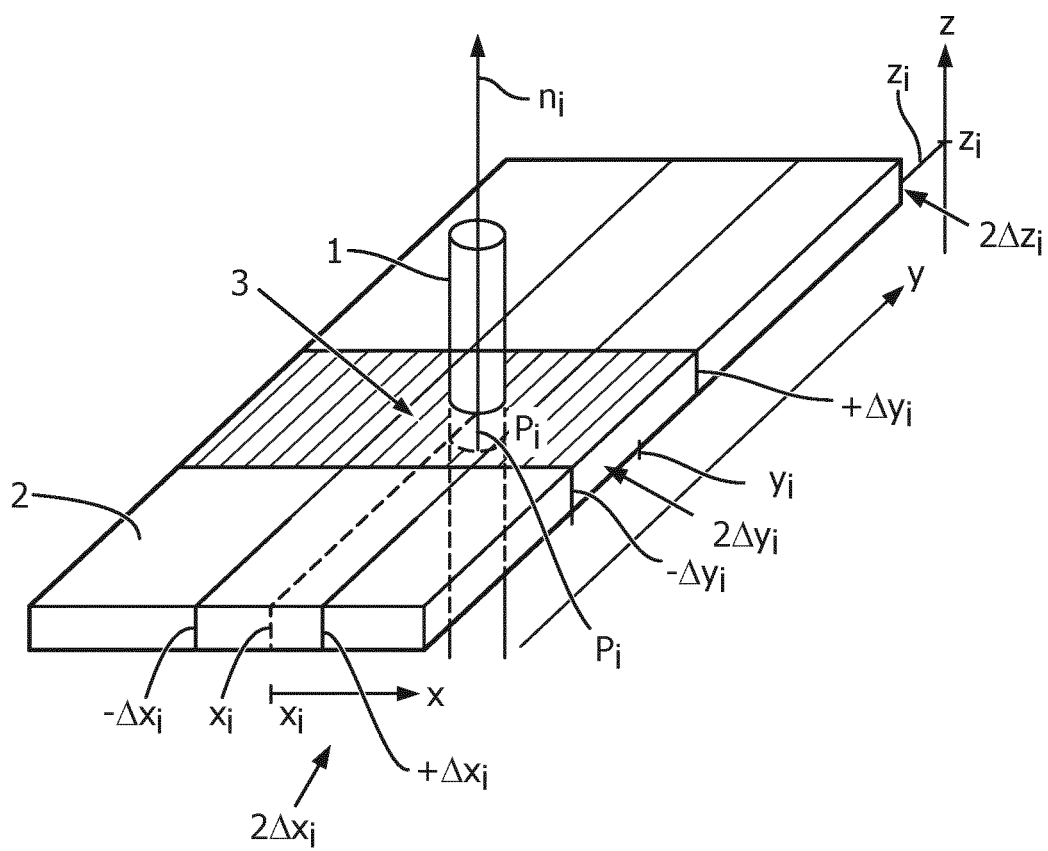
FIG. 1 schematically depicts a sketch of an invasive device with point $P_i$ at a position $x_i$, $y_i$, $z_i$ localized by an optical shape sensing system and an excited z-slice in accordance with an embodiment of the invention.

FIG. 1 schematically depicts a sketch of an invasive device 1 with point $P_i$ at a position $x_i$, $y_i$, $z_i$ localized by an optical shape sensing system and an excited z-slice 2 in accordance with an embodiment of the invention. A point $P_i$ is localized by FORS on the invasive device 1 to be at the position $x_i$, $y_i$, $z_i$ but due to limited accuracy the true location may be contained in an error margin $2\Delta x_i$, $2\Delta y_i$, $2\Delta z_i$ centered at $x_i$, $y_i$, $z_i$, wherein the size of this error margin $2\Delta x_i$, $2\Delta y_i$, $2\Delta z_i$ may vary per point and is therefore indexed and without further prior knowledge the size will generally increase towards the tip of the invasive device 1. The FORS reconstruction also provides the direction vector $n_i$ of the invasive device 1 at point $P_i$. In order to improve the accuracy of localization of $P_i$ in x-direction x the MR scanner measures the position $x_i$, $y_i$, $z_i$ of the point $P_i$ on the invasive device 1. In an embodiment of the invention, it may in particular be provided that the MR scanner excites a slice 2 of about two to three times the thickness of the invasive device 1 centered at $x_i$, $y_i$, $z_i$ and perpendicular to the direction vector $n_i$ as sketched in FIG. 1. A readout of signal of that slice 2 with a readout gradient along the x-direction x provides a projection of all signal in that slice 2 integrated along the y-direction y. Due to the absence of water in the invasive device 1 a small signal reduction is expected in this projection at the true position $x_{ti}$ of the device. However, the heterogeneity of the signal from body tissue in the entire slice 2 will also provide signal variations so that the small signal reduction by the invasive device 1 will likely be obscured. Therefore, the signal from the slice 2 outside the region $y_i-\Delta y_i$ to $y_i+\Delta y_i$ is proposed to be suppressed before signal readout. As a result, the projection contains only signal integrated along y in that small region. The absence of signal in the device will now result in a significant signal reduction in the projection. The position of this signal dip corresponds to the true position $x_{ti}$ of the device. The search for this signal dip only needs to be performed in a region $x_i-\Delta x_i$ to $x_i+\Delta x_i$ due to the prior knowledge from the FORS measurement. The signal suppression can be performed by various schemes.

In an embodiment of the invention the signal suppression is performed by a spin echo-scheme. After a z-slice-selective excitation a y-slice-selective refocusing pulse is performed with slice center at $y_i$, and slice thickness of $2\Delta y_i$. The following readout in x-direction x will only acquire signal from the cross section of the excitation z-slice 2 and the refocusing y-slice. In another embodiment the signal suppression is performed by a saturation-scheme, wherein a signal in regions outside $y_i-\Delta y_i$ to $y_i+\Delta y_i$ is excited and spoiled, followed by the z-slice 2 selective excitation and readout along x-direction x.

In a further embodiment of the invention the signal suppression is performed by a 2d-excitation scheme. A 2d-pulse is used to excite only a column of signal along x, centered at $x_i$, $y_i$, $z_i$ and with width $y_i$, $z_i$. For illustration and ease of annotation, the invasive device 1 has been oriented along the z-axis z in FIG. 1. The approximate orientation of the invasive device 1 at point $P_i$ can be derived from the FORS data to orient the selection slice 2 perpendicular to the invasive device 1. This results in minimal partial volume effects caused by the finite width of slice 2 and pixels in the projection read-out.

The above embodiment of the invention describes the acquisition of MR projection data to improve the localization of $P_i$ in x-direction x. To improve the localization also in y- and z-direction y, z in an embodiment of the invention analog steps can be performed in at least another spatial direction x, y, z.

The direction along the invasive device 1, in the embodiment shown in FIG. 1 the z-direction z, represents a slightly different problem because the invasive device 1 a priori does not provide structures that can be visualized in MR. However, points $P_i$ may be chosen to coincide with structures of the invasive device 1 that already provide some MR contrast. In another embodiment of the invention points $P_i$ may be equipped with passive MR markers known in the art to provide sufficient MR contrast. Passive MR markers are paramagnetic, ferromagnetic, ferrimagnetic and antiferromagnetic metals, metal alloys and metal compounds. They are preferably embedded as particles in a plastic matrix. In addition, active markers like resonant pickup radiofrequency (RF) coils or semi-active inductively coupled RF coils can be provided. Even with only the $x_i$ and $y_i$ co-ordinates of point $P_i$ the localization of FORS is improved. As a result of the MR measurements, the true positions of points $P_i$ are available at a high accuracy. Therefore, the FORS reconstruction can be done segment per segment and just must solve for the shapes between those points. Initially, MR localization of the tip of the invasive device 1 results in the largest gain of information with respect to the FORS reconstruction. In an embodiment it is may be intended to firstly localize the tip point of the invasive device 1 with MR and to continue with a point at half the length of the invasive device 1, then at quarter length and so forth as in a half-interval search.

Figure 2:
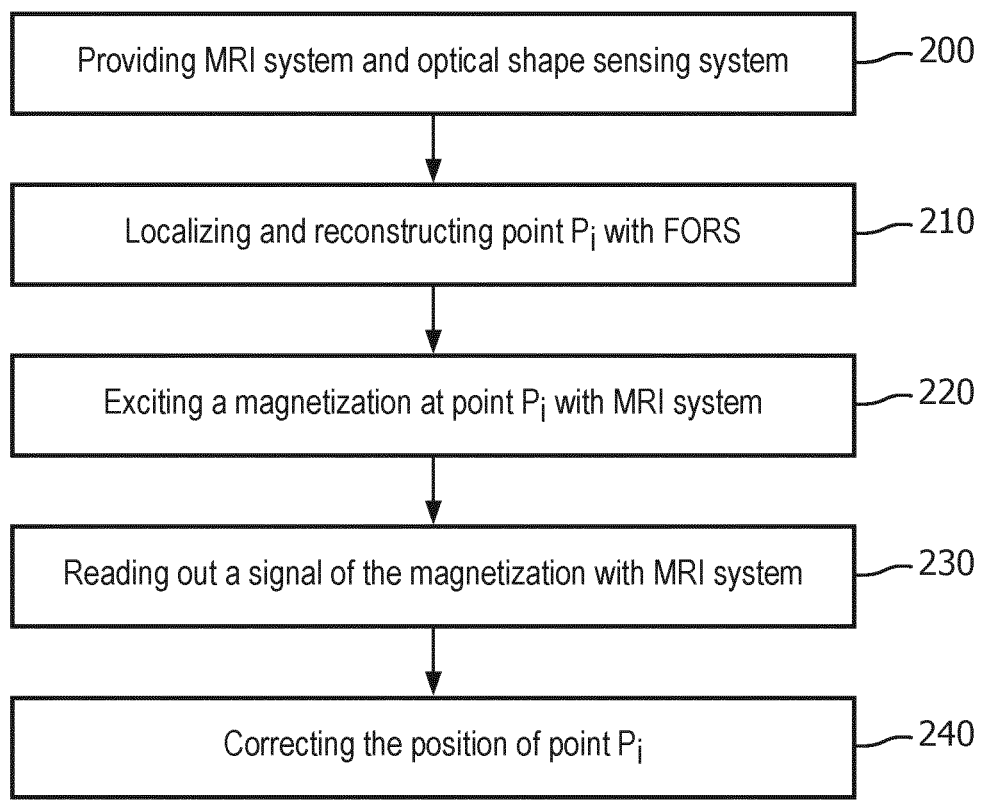
FIG. 2 shows a flowchart of a method for determining the position of an invasive device in accordance with an embodiment of the invention.

FIG. 2 shows a flowchart of a method for determining the position of an invasive device 1 in accordance with an embodiment of the invention. The method starts with step 200 by providing at least one invasive device 1, a magnetic resonance imaging (MRI) system and an optical shape sensing system. The optical shape sensing system is configured for determining a position and/or shape of the invasive device 1. Optical shape sensing or fiber-optical shape sensing allows sensing the shape of a flexible compound optical fiber in 3D with high temporal and spatial resolution. It is based on optical sensing of the strain of individual optical cores along the compound fiber, either by fiber Bragg gratings or by Rayleigh scattering. The known relative configuration of the cores allows reconstruction the shape of the compound fiber from the strain data.

In step 210 at least one point $P_i$ on the invasive device 1 at a position $x_i$, $y_i$, $z_i$, is localized and reconstructed by the optical shape sensing system with some error margin $2\Delta x_i$, $2\Delta y_i$, $2\Delta z_i$ in a region of interest 3.

In step 220 a magnetization is excited in the error margin $2\Delta x_i$, $2\Delta y_i$, $2\Delta z_i$ in the region of interest 3 at least in one spatial direction x, y, z by the MRI system. In an embodiment of the invention the magnetization can be excited as a z-slice and/or a y-slice and/or a x-slice 2 centered at the point $P_i$ at a position $x_i$, $y_i$, $z_i$ and perpendicular to a direction vector $n_i$ of the invasive device 1 with the MRI system. In order to improve the accuracy of localization of $P_i$ e.g. in x-direction x the MR scanner excites a slice 2 of about two to three times the thickness of the invasive device 1 centered at $x_i$, $y_i$, $z_i$ and perpendicular to the direction vector $n_i$. Therefore, in an embodiment of the invention it can be foreseen to derive the approximate orientation of the invasive device 1 at point P from the FORS data and to orient the selection slice 2 perpendicular to the invasive device 1. This results in minimal partial volume effects caused by the finite width of slice and pixels in the projection read-out.

In step 230 a signal of the magnetization in the error margin $2\Delta x_i$, $2\Delta y_i$, $2\Delta z_i$ is read out by the MRI system. In an embodiment of the invention the signal of the excited z-slice and/or a y-slice and/or a x-slice 2 with a readout gradient along the x-direction x and/or along the y-direction y and/or along the z-direction z is read out by the MRI system. For example a readout of signal of a slice 2 with a readout gradient along the x-direction x provides a projection of all signal in that slice 2 integrated along the y-direction y. Due to the absence of water in the device a small signal reduction is expected in this projection at the true position of the device $x_{ti}$. However, the heterogeneity of the signal from body tissue in the entire slice will also provide signal variations so that the small signal reduction by the device will likely be obscured. Therefore, the signal from the slice 2 outside the region $y_i-\Delta y_i$ to $y_i+\Delta y_i$ is proposed to be suppressed before signal readout. As a result, the projection contains only signal integrated along y in that small region. The absence of signal in the device will now result in a significant signal reduction in the projection. The position of this signal dip corresponds to the true position $x_{ti}$ of the invasive device 1. The search for this signal dip only needs to be performed in a region $x_i-\Delta x_i$ to $x_i+\Delta x_i$ due to the prior knowledge from the FORS measurement. Therefore, in a further embodiment of the invention the step of determining a position of the invasive device 1 based on the signal comprises the step of performing a scheme for signal suppression of the signal of the excited z-slice and/or a y-slice and/or a x-slice 2 outside a region $x_i-\Delta x_i$ to $x_i+\Delta x_i$ and/or $y_i-\Delta y_i$ to $y_i+\Delta y_i$ and/or $z_i-\Delta z_i$ to $z_i+\Delta z_i$ based on the localizing and reconstructing of the at least one point $P_i$ on the invasive device 1 at the position $x_i$, $y_i$, $z_i$ by the optical shape sensing system.

The signal suppression can be performed by various schemes. For example, the step of performing a scheme for signal suppression of the signal of the excited z-slice and/or a y-slice and/or a x-slice 2 is performed by a spin echo scheme comprising the following steps:

selective exciting a z-slice and/or y-slice and/or x-slice 2,
performing a selective y-slice refocusing pulse with a slice center at $y_i$ and a slice thickness of $2\Delta y_i$ and/or performing a selective x-slice refocusing pulse with a slice center at $x_i$ and a slice thickness of $2\Delta x_i$ and/or performing a selective z-slice refocusing pulse with a slice center at $z_i$ and a slice thickness of $2\Delta z_i$
reading out the signal along the x-direction x, and/or z-direction z and/or y-direction y.

In another embodiment of the invention the step of performing a scheme for signal suppression of the signal of the excited z-slice and/or a y-slice and/or a x-slice 2 is performed by a saturation scheme comprising the following steps:

exciting and spoiling a signal in a region outside $y_i-\Delta y_i$ to $y_i+\Delta y_i$ and/or $x_i-\Delta x_i$ to $x_i+\Delta x_i$ and/or $z_i-\Delta z_i$ to $z_i+\Delta z_i$,
selective exciting a z-slice and/or y-slice and/or x-slice 2,
reading out the signal along the x-direction x and/or z-direction z and/or y-direction y.

In a further embodiment of the invention the step of performing a scheme for signal suppression of the signal of the excited z-slice and/or a y-slice and/or a x-slice 2 is performed by a 2d-excitation scheme comprising the following steps:

exciting a column of a signal along x-direction x and/or y-direction y and/or z-direction z by a 2d-pulse centered at the point $P_i$ at the position $x_i$, $y_i$, $z_i$.

The measured data obtained in this way are then used for determining a position of the invasive device 1 based on the signal.

In step 240 the position $x_i$, $y_i$, $z_i$, of the point $P_i$ on the invasive device 1 in the region of interest 3 determined by the optical shape sensing system is corrected with the position $x_i$, $y_i$, $z_i$, of the point $P_i$ on the invasive device 1 in the region of interest 3 determined by the MRI system by the calculating system to an actual position of the invasive device 1.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope. Further, for the sake of clearness, not all elements in the drawings may have been supplied with reference signs.

REFERENCE SYMBOL LIST invasive device 1
excited slice by the MRI system 2
region of interest 3
point $P_i$ at position $x_i$, $y_i$, $z_i$ $P_i$
direction vector of the invasive device $n_i$
spatial direction x, y, z
error margin around point $P_i$ $2\Delta x_i$, $2\Delta y_i$, $2\Delta z_i$

The invention claimed is:

1. An arrangement for determining a position of an invasive device, the arrangement comprising:
    the invasive device,
    an optical shape sensing system, wherein the optical shape sensing system is configured for determining at least one of the position of the invasive device or a shape of the invasive device, the optical shape sensing system further being arranged to localize and reconstruct a point on the invasive device at the position with an error margin in a region of interest,
    a diagnostic imaging system comprising a magnetic resonance imaging (MRI) system, wherein the diagnostic imaging system is configured to measure the position of the point on the invasive device within the error margin in the region of interest in at least one spatial direction, to excite a magnetization in the error margin in the region of interest in the at least one spatial direction by exciting at least one of a z-slice to be an excited z-slice, a y-slice to be an excited y-slice, or an x-slice to be an excited x-slice centered at the point at the position and perpendicular to a direction vector with the MRI system, the MRI system being arranged to read out a signal of the excited z-slice, the excited y-slice, or the excited x-slice with a readout gradient along at least one of the at least one spatial direction, the MRI system further being arranged to find a signal suppression in the signal of the excited z-slice, the excited y-slice, or the excited x-slice to determine the position of the point on the invasive device based on the signal of the excited z-slice, the excited y-slice, or the excited x-slice, and
    a calculating system, wherein the calculating system is configured to correct the position of the point on the invasive device determined by the optical shape sensing system by the position, of the point on the invasive device determined by the diagnostic imaging system.

2. The arrangement according to claim 1, wherein the invasive device comprises a magnetic resonance (MR) marker along an extension of the invasive device.

3. The arrangement according to claim 2, wherein the MR marker is at least one selected from a list consisting of: paramagnetic agents, ferromagnetic agents, ferrimagnetic agents, antiferromagnetic agents, resonant pickup radiofrequency (RF) coils, or inductively coupled RF coils.

4. The arrangement according to claim 3, wherein when exciting the magnetization in the error margin in the region of interest has been performed in a first spatial direction by the MRI system, the MRI system is further configured to excite another magnetization in the error margin in the region of interest in at least another spatial direction.

5. A method for determining a position of an invasive device, the method comprising:
providing the invasive device
providing a diagnostic imaging system comprising a magnetic resonance imaging (MRI) system,
providing an optical shape sensing system for sensing at least one of the position of the invasive device or a shape of the invasive device, the optical shape sensing system being arranged to localize and reconstruct a point on the invasive device at the position with an error margin in a region of interest,
measuring the position of the point on the invasive device within the error margin in the region of interest in at least one spatial direction by the diagnostic imaging system by exciting at least one of a z-slice to be an excited z-slice, a y-slice to be an excited y-slice or an x-slice to be an excited x-slice centered at the position of the point and perpendicular to a direction vector of the invasive device with the diagnostic imaging system, reading out a signal of the excited z-slice, the excited y-slice, or the excited x-slice within the error margin by the diagnostic imaging system, and determining the position of the invasive device based on the signal,
correcting the position of the point on the invasive device in the region of interest determined by the optical shape sensing system with the position of the point on the invasive device in the region of interest determined by the diagnostic imaging system.

6. The method according to claim 5, wherein the reading out of the signal of the excited z-slice, the excited y-slice, or the excited x-slice within the error margin of the diagnostic imaging system is performed with a readout gradient along at least one of the at least one spatial direction.

7. The method according to claim 5, wherein determining the position of the invasive device based on the signal of the excited z-slice, the excited y-slice, or the excited x-slice comprises performing a scheme for signal suppression of the signal of the excited z-slice, the excited y-slice or the excited x-slice outside the region of interest based on the point on the invasive device at the position by the optical shape sensing system.

8. The method according to claim 7, wherein performing the scheme for signal suppression of the signal of the excited z-slice, the excited y-slice, or the excited x-slice is performed by a spin echo scheme.

9. The method according to claim 7, wherein performing the scheme for signal suppression of the signal of at least one of the excited z-slice, the excited y-slice, or the excited x-slice is performed by a saturation scheme.

10. The method according to claim 7, wherein performing the scheme for signal suppression of the signal of the excited z-slice, the excited y-slice or the excited x-slice is performed by a two-dimensional excitation scheme.

11. The method according to claim 5, wherein the invasive device comprises a magnetic resonance (MR) marker along an extension of the invasive device.

12. The method according to claim 5, wherein the point is at a tip point of the invasive device or along a shaft of the invasive device.

13. A computer program product comprising instructions stored on non-transitory computer readable medium which, when the program is executed by a computer comprising a calculating system, cause the computer to carry out a method of:
sensing, using an optical shape sensing system, at least one of a position of an invasive device, or a shape of the invasive device, the optical shape sensing system being arranged to localize and reconstruct a point on the invasive device at the position with an error margin in a region of interest,
measuring, by a diagnostic imaging system comprising a magnetic resonance imaging (MRI) system, the position of the point on the invasive device within the error margin in the region of interest in at least one spatial direction by exciting at least one of a z-slice to be an excited z-slice, a y-slice to be an excited y-slice or an x-slice to be an excited x-slice centered at the position of the point and perpendicular to a direction vector of the invasive device with the diagnostic imaging system, reading out a signal of the excited z-slice, the excited y-slice, or the excited x-slice within the error margin by the diagnostic imaging system, and determining the position of the invasive device based on the signal, and
correcting, by the calculating system, the position of the point on the invasive device in the region of interest determined by the optical shape sensing system with the position of the point on the invasive device in the region of interest determined by the diagnostic imaging system.

* * * * *